United States Patent [19]

Kramer et al.

[11] Patent Number: 4,683,887
[45] Date of Patent: Aug. 4, 1987

[54] AIR CIRCULATION SYSTEM FOR A TANNING SYSTEM

[76] Inventors: Sharon D. Kramer, Rte. 6, Box 233; John Kramer, 806 Lynn Pl.; Donald Kramer, 9913 W. Meadowbrook; Clark Kramer, Rte. 6, Box 255K, all of Yakima, Wash. 98907

[21] Appl. No.: 865,178

Related U.S. Application Data

[62] Division of Ser. No. 642,565, Oct. 14, 1985, Pat. No. 4,600,009.

[22] Filed: May 19, 1986

[51] Int. Cl.$^4$ .......................... A61N 5/06; F21V 29/00
[52] U.S. Cl. .................................... 128/376; 362/218; 128/396
[58] Field of Search ................ 128/376, 395, 396; 362/218

[56] References Cited

U.S. PATENT DOCUMENTS

| | | | |
|---|---|---|---|
| 3,173,616 | 3/1965 | Lipscomb | 362/218 |
| 3,183,346 | 5/1965 | Spaulding et al. | 362/218 |

FOREIGN PATENT DOCUMENTS

| | | | |
|---|---|---|---|
| 2848234 | 9/1979 | Fed. Rep. of Germany | 128/396 |
| 2831013 | 1/1980 | Fed. Rep. of Germany | 128/396 |
| 3005487 | 8/1981 | Fed. Rep. of Germany | 128/395 |
| 3123378 | 1/1983 | Fed. Rep. of Germany | 128/396 |

Primary Examiner—Anton O. Oechsle
Attorney, Agent, or Firm—Seed and Berry

[57] ABSTRACT

Improvements in the air circulatory system, counterbalance system, an integrally contained facial tanning unit and an audio console, all of which form components of an ultraviolet light generating tanning system, are disclosed. The air circulatory system utilizes cooling air intake vents, a series of exit fans and a pair of channeled panels having a plurality of apertures formed therein. A series of air baffles or dams are mounted beneath the panels. The facial tanning unit utilizes a series of separate facial ultraviolet lamps, each operatively connected to a separate ballast. The counterbalance system uses a pair of pivot arms mounted in parallel fashion, an axle coupled to and extending between each of the arms, and a pair of torsion springs, each of which is wound around and offset from opposite ends of the axle. The audio console has a housing shaped to match the contours of the tanning system and utilizes a set of controls positioned in an inverted fashion for greater accessibility.

8 Claims, 10 Drawing Figures

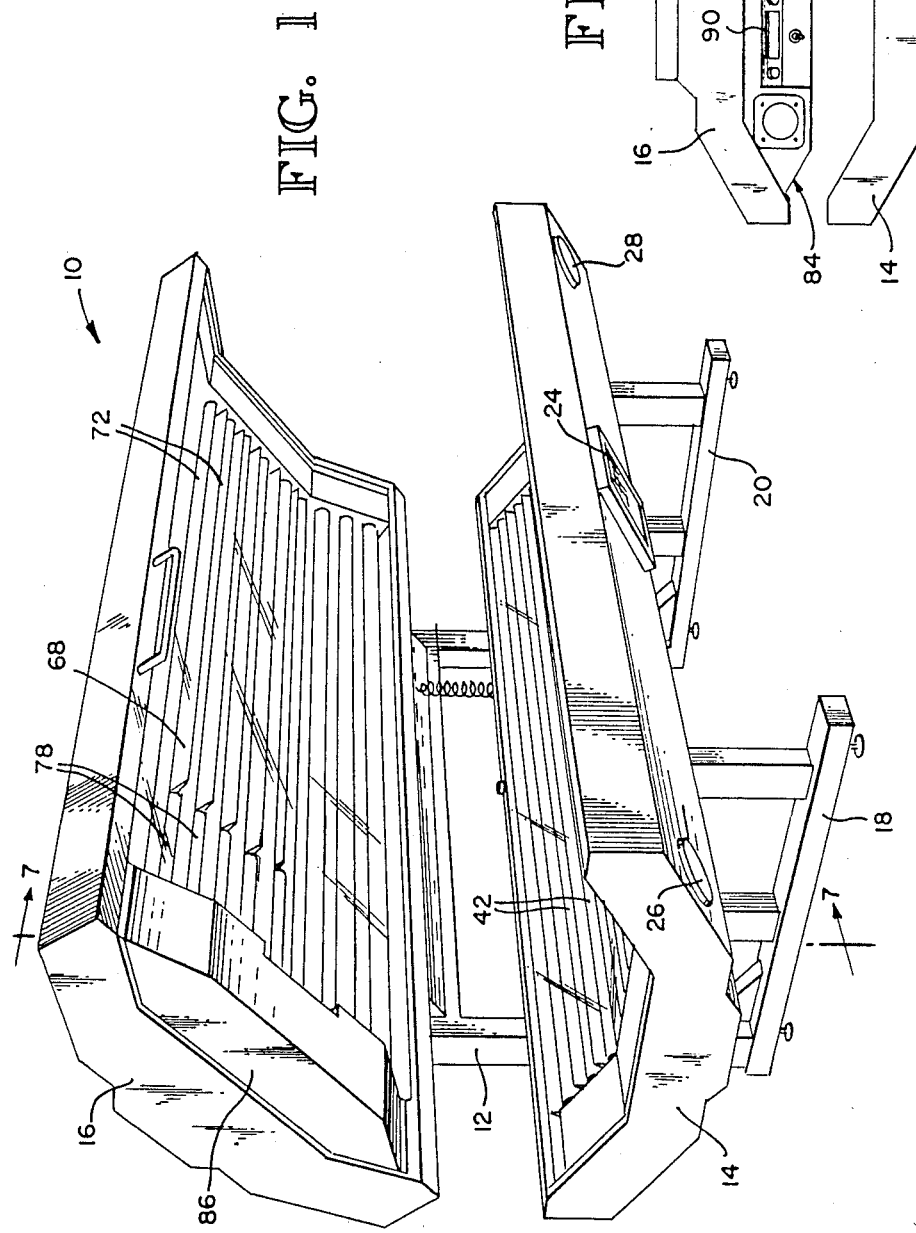

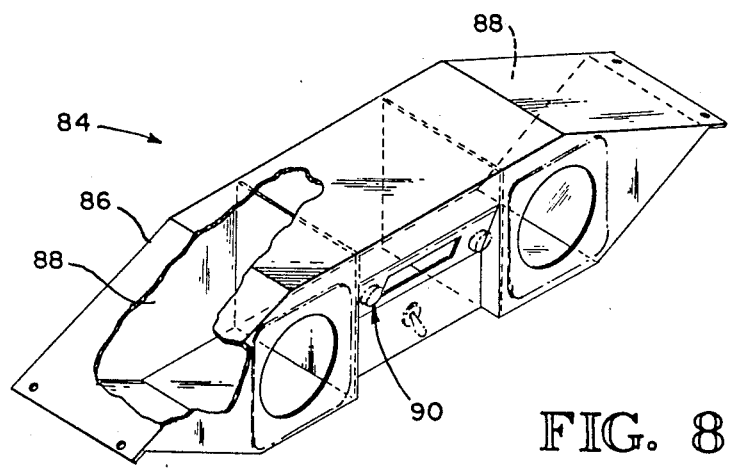
FIG. 8
FIG. 9
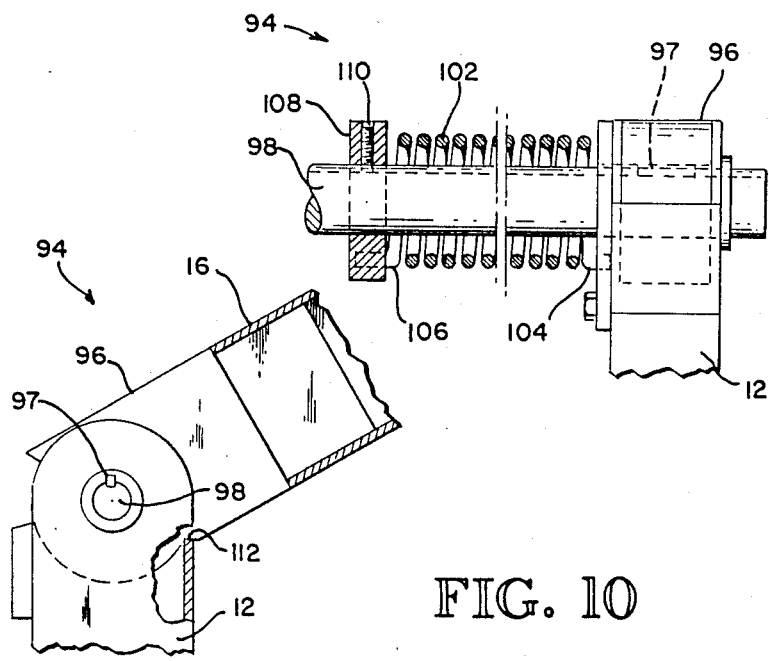
FIG. 10

4,683,887

AIR CIRCULATION SYSTEM FOR A TANNING SYSTEM

This application is a divisional of U.S. patent application Ser. No. 642,565, filed Oct. 14, 1985, now U.S. Pat. No. 4,600,009.

DESCRIPTION

1. Technical Field

The present invention relates to ultraviolet light tanning systems in general, and more specifically, to improvements of those tanning systems related to the air circulation, lid weight counterbalancing, integral facial tanning unit, and an integral audio console.

2. Background Art

Providing an effective and efficient method of maintaining the temperature of ultraviolet light lamps within a limited range (90°–110° F.) has long been a concern of manufacturers of ultraviolet (U.V.) light tanning systems. If the operating temperature of the lamp exceeds a certain limit, the ratio of the output of U.V. alpha rays (U.V.A.) to U.V. beta rays (U.V.B) will be disrupted, causing the U.V.B. output of the lamps to dangerously increase. In addition, the maintenance of a proper bulb temperature maximizes U.V. lamp life, as well as minimizing the radiant heat transfer from the lamp to a person positiond within the tanning bed or lounge.

The conventional method of cooling a series of U.V. lamps within a tanning bed or lounge has been to flush air from one end of the bed or lounge along the length thereof to the other end, where it is drawn out through one or more exit fans. However, this is disadvantageous in that a severe temperature gradient is created along the length of the lamps, thereby causing an uneven output of U.V.A. and U.V.B. ultraviolet light rays.

In addition to inadequate cooling systems, the existing tanning systems have not effectively addressed the problem of simultaneously and evenly tanning an individual's face concurrently with the rest of his or her body. Since an individual usually wants a darker tan on the face, it has been necessary in the past for a person to utilize a separate facial tanning unit before or after utilizing the tanning bed or lounge itself.

Further, once an individual enters and lies down on the lower surface of a tanning bed or lounge, he or she is faced with the problem of conveniently positioning the upper portion of the unit so that the system may operate properly. In the past, tanning beds or lounges have been provided with a set of damper cylinders which act to hold the upper portion of the unit in place. This is disadvantageous, however, due to the physical effort required to overcome the frictional resistance of the cylinders and the weight of the upper portion.

In addition to the problems associated with conventional tanning beds or lounges as noted above, there is also the problem of providing an environment within the bed or lounge which is both entertaining and relaxing. In particular, the use of audio systems which generate superior sound quality have been noticeably absent from tanning lounges or beds in the past.

Consequently, there exists a need in the art for an improved tanning system which provides features which effectively eliminate the disadvantages noted above, as well as providing other related advantages.

DISCLOSURE OF INVENTION

Briefly stated, the present invention provides a series of improvements in the air circulatory system, counterbalance system, integrally contained facial tanning unit, and audio console, all of which form components of an ultraviolet light generating tanning system.

One aspect of the invention provides an improved air circulatory system which utilizes intake vents centrally located along the length of the unit, a series of exit fans which are positioned toward the ends of the upper and lower units and adapted to draw air out of the interior of those units, and a pair of channeled panels having a plurality of apertures formed therein and positioned to longitudinally extend along the interior of the upper and lower units, the channels corresponding in position to and aligned with the ultraviolet light lamps contained within the tanning system. Preferably the apertures are precisely located to direct air flow to the areas in the units which are subjected to the maximum heat generation to provide a uniform operating temperature for all parts of the lamps. Also, a series of air baffles or dams is preferably mounted beneath the channeled panels and is adapted to direct air flowing substantially toward the longitudinal center of the upper and lower units. The baffles enhance flow from naturally cooler areas of the units to higher heat source areas such as at the location of the lamp ballasts.

Another aspect of the invention provides a facial unit which forms an integral part of the tanning system. The facial unit essentially consists of a substantially rectangular plate which is mounted onto and toward one end of the system. The plate has a series of apertures formed therein, and a second series of smaller facial U.V. light generating lamps are positioned on the plate between the regular long body tanning lamps. Each of the smaller facial lamps is operatively connected to a separate ballast positioned within the tanning system for more stable excitation of the lamps.

A further aspect of the invention provides a counterbalance system for use with a tanning bed or lounge having a pivotable upper unit and a stationary lower unit secured to a frame. The counterbalance affects the weight of the upper unit so that only a few pounds of force is needed to move a 185 lb. top unit and friction will allow the counterbalanced unit to remain fixed in any position. The system uses a pair of pivot arms mounted in parallel fashion to substantially opposite ends of the upper unit, an axle coupled to and extending between each of the arms, and a pair of torsion springs, each of the springs wound around and offset from opposite ends of the axle. One end of each spring is connected to an arm and the other end is fixed to the frame.

The invention also provides an audio console adapted for use within a U.V. tanning system. The console generally comprises a housing having a substantially rigid and excellent acoustic chamber configuration for the speakers. The housing is shaped to match the contours of the upper unit so that it fits within the upper unit for accessibility by the user while in the tanning unit. A set of controls is positioned in an inverted fashion for more accessibility to an individual positioned in the tanning system. As contrasted to ear phone systems or remote sound systems that cannot be heard over the tanning system air fans, this integral sound system provides excellent stereo acoustics adjacent to the user's head and provides controls readable and usable by a person lying in the tanning system.

BRIEF DESCRIPTION OF THE DRAWINGS

FIG. 1 is an isometric view of a tanning system embodying the present invention.

FIG. 2 is a fragmentary end elevational view of the system of FIG. 1.

FIG. 8 is a fragmentary isometric view of an audio console of the tanning system of FIG. 1.

FIG. 9 is a fragmentary front elevation of a portion of the system.

FIG. 10 is a fragmentary end elevation of a portion of the system.

BEST MODE FOR CARRYING OUT THE INVENTION

Figure 3:
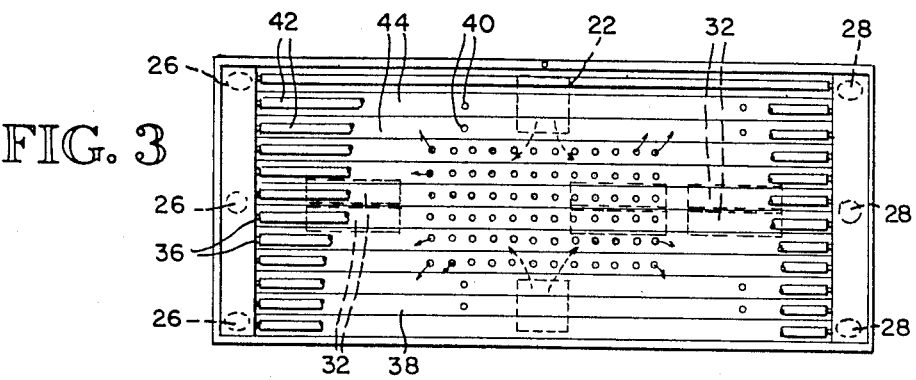
FIG. 3 is a fragmentary view of a lower unit of the tanning system of FIG. 1.

In reference to FIG. 1, an ultraviolet light tanning system 10 is generally comprised of a frame 12 upon which is mounted a lower unit 14 and an upper unit 16. The frame 12 is formed from a pair of L-shaped members 18 and 20, each of the members being positioned toward opposite ends of the upper and lower units in order to provide stability. The L-shaped members 18 and 20 are preferably made of rust-proof, lightweight aluminum for strength and durability.

The U.V. tanning system 10 incorporates an improved air circulatory system, an integral tanning system, a counterbalance system for maintaining the upper unit 16 in proper position while allowing the upper unit to be raised or lowered with negligible physical effort, and an audio console adapted for use within the tanning system.

AIR CIRCULATORY SYSTEM

Figure 4:
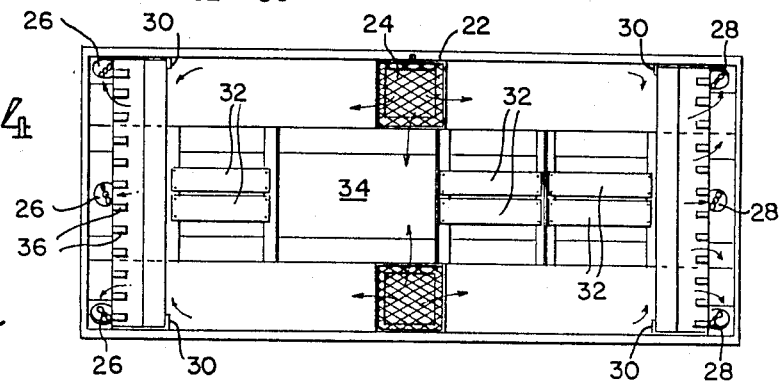
FIG. 4 is a view of a lower unit of the tanning system of FIG. 1 exposing the interior of the unit.

As shown in FIG. 4, mounted on the underside of the lower unit 14 is a pair of air intake vents 22 having removable metallic screens 24. Due to dust which is naturally attracted to the U.V. lamps within the system, it is preferable to provide the intake vents 22 with removable air filters which can be rinsed off and replaced. As shown by the arrows in FIG. 4, air is drawn in through the intake vents by a series of exit fans 26 and 28. The exit fans 26 and 28 are also located on the underside of the lower unit and may be provided with removable metal screens. In order to draw an optimum volume of air through the lower unit, it is preferable to utilize a series of six fans, three evenly spaced at each end, each having a capacity of approximately 105 cfm.

Air drawn from the intake vents 22 toward the fans 26 and 28 is directed inward toward the longitudinal center of the lower unit. The air divides and flows toward each end of the unit, providing a shorter air cooling path and thus a lower temperature gradient along the length of the lamps. Air baffles or dams 30 direct a greater volume of air toward the heat generating ballasts 32 positioned along the longitudinal center of the lower unit, thereby dissipating the radiant heat generated by the ballasts. Through efficient cooling of the ballast and increased air flow to the center more concentrated heat generating lamps, the creation of a concentration of heat at the lamps is avoided, thereby maximizing U.V. lamp life as well as ensuring that the bulbs operate at a safe, uniform temperature. The ballasts 32 are spaced in the lower unit such that a void 34 is created near the center of the lower unit, extending toward one end. This arrangement is preferable to reduce the amount of heat from the ballasts that could reach the more sensitive portions of the human anatomy, such as the buttocks, which are normally clothed within a swimsuit and thus are more sensitive to the U.V. rays. As air flows over the ballasts and toward the ends of the lower unit 14, the air is diverted under and between a series of U.V. bulb sockets 36.

Referring now to FIG. 3, positioned to extend along but remain offset from the interior of the lower unit 14 is a channeled panel or screen 38. The panel 38 is provided with a plurality of apertures 40 that guide air which has entered the lower unit through the intake vents to circulate along a series of long body U.V. bulbs 42 in order to cool them. The U.V. bulbs 42 are positioned in a series of channels 44. The channels 44 are provided for reflecting the rays as is well known. The apertures 40 are positioned along the length of the U.V. lamps to increase air flow to the central lamps (in the higher heat area) and to the longitudinal center (where the most sensitive body portion will rest), thereby aiding in the maintenance of a suitable operating temperature for the lamps. Consistent with this arrangement, relatively few apertures are located on the transverse and longitudinal outermost channel areas.

The U.V. lamps 42 and the channeled screen 38 are protected and remain out of direct contact with an individual positioned upon the lower unit by means of a lamp cover 48 sold under the trademark PLEXIGLAS which is substantially clear and extends the full length of the lower unit.

As an additional measure to cool the ballasts 32 (FIG. 7) the lower surface of the ballasts abut the highly conductive aluminum shell 46 in the lower unit which assists in dissipating the heat generated by the ballasts 32. The shell 46 forms a heat sink to increase cooling as opposed to relying solely on a stream of air flowing over the surface of the ballasts.

Figure 6:
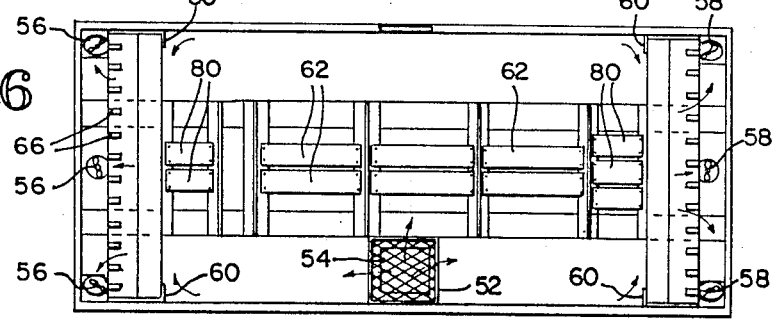
FIG. 6 is a view of an upper unit of the tanning system of FIG. 1 exposing the interior of the unit.

Referring now to FIG. 6, mounted within the upper unit 16 is a single intake vent 52 positioned on the top side and toward the rear of the upper unit so that it is relatively inaccessible to an individual utilizing the tanning system, making it less likely that any foreign objects will be dropped into the interior of the upper unit. The intake vent 52 may be provided with a removable metallic grid 54. As mentioned previously, dust is naturally attracted to the U.V. lamps within the system, and therefore it is preferable to provide the intake vent 52 with a removable air filter which may be rinsed off and then replaced. As shown by the arrows within FIG. 6, air is drawn into the upper unit through the intake vent 52 by a series of exit fans 56 and 58. The exit fans 56 and 58 are located on the top side of the upper unit and may be provided with removable metal screens in order to insure that foreign objections do not interfere with their operation In order in draw an optimum volume of air through the upper unit, it is preferable to utilize a series of six fans, three evenly spaced at each end, each with a capacity of approximately 105 cfm.

Air drawn from the intake vent 52 toward the fans 56 and 58 is directed inwardly toward the longitudinal center of the upper unit. Air dams or baffles 60 also assist in guiding air to the central lamps. As shown by the arrows in FIG. 6, the position of the air dams directs a greater volume of air over the surface of a series of heat generating ballasts 62. Through efficient cooling of the ballasts, the creation of a concentration of heat at the lamps is avoided, thereby maximizing U.V. lamp life as well as ensuring that the lamps operate a proper temperature. As air flows over the ballasts and toward the ends of the upper unit 16, it is directed beneath and between a series of U.V lamp sockets 66.

Figure 5:
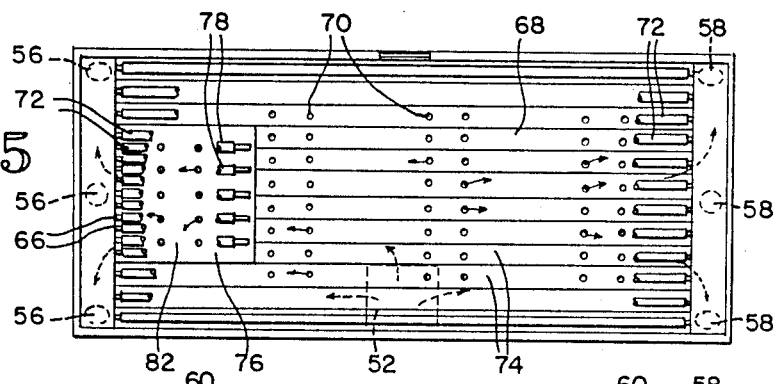
FIG. 5 is a fragmentary view of an upper unit of the tanning system of FIG. 1.

Referring now to FIG. 5, positioned to extend along but remain offset from the interior of the upper unit 16 is a channeled panel or screen 68. The panel 68 is provided with a plurality of apertures 70 to allow air which has entered the upper unit through the intake vent to circulate along a series of U.V. lamps 72 positioned in a series of channels 74. The channels 74 function to guide the flow of air along the length of the U.V. lamps, thereby aiding in the maintenance of a suitable operating temperature for the bulbs.

It is preferable to spatially arrange the apertures 70 in the manner depicted so as to increase air flow over the lamps in the central higher heat generating area of the unit and thus maintain an even temperature along the surface of the lamps 72. Preferably the apertures are in three uniform sets with additional apertures at the facial unit. The particular patterns in both the upper and lower unit have been found uniquely suited to maintain a substantially uniform temperature along the lamps.

Figure 7:
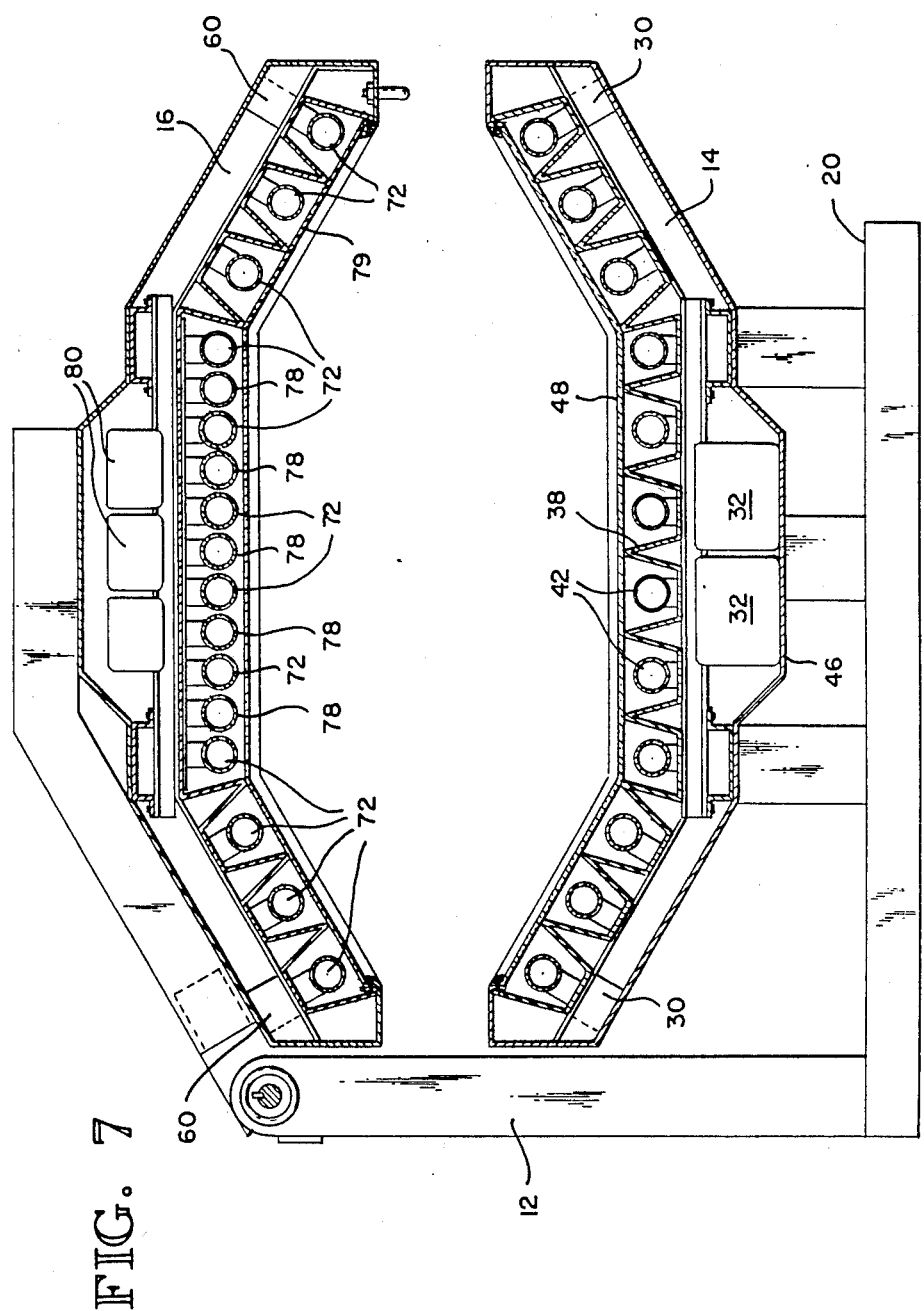
FIG. 7 is an end elevational view of the system of FIG. 1.

The U.V. bulbs 72 and the channeled screen 68 are protected and remain out of direct contact with an individual positioned within the tanning system through a clear covering 79 sold under the trademark PLEXIGLAS, best shown in FIG. 7, which extends the length of the surface of the upper unit 16.

INTEGRAL FACIAL TANNING UNIT

Referring again to FIG. 5, mounted within and forming an integral part of the upper unit 16 is a facial tanning unit 76 which is positioned to lie directly above an individual's face when he or she is positioned within the tanning system. As shown in FIG. 5 the facial unit 76 utilizes a series of short U.V. lamps 78 interspersed among the U.V. lamps 72. Each of the U.V. lamps 78 is individually driven by one of a series of ballasts 80 positioned on the upper unit 16. By utilizing a single ballast to drive each of the U.V. lamps 78, a stable light emission of greater intensity is achieved, resulting in a peak output of U.V.A and a minimum of U.V.B. It is preferable to arrange the ballasts 80 such that three are located at the end distal from the facial unit while two are located at the same end as or proximal with the facial unit in order to reduce the radiant heat from the ballasts generated at the end of the upper unit directly over the head of an individual positioned within the tanning system. For one example, the facial unit increases U.V.A. by about 30%-40% while the U.V.B. stayed at less than 0.05% of the total U.V.A. and U.V.B. radiation.

Between the U.V. bulbs 78 and ballasts 80 is a substantially rectangular plate 82. The plate 82 is provided with a plurality of apertures 84 formed therein to allow air which has entered the upper unit through the intake vent to circulate among the U.V. lamps 78. It is preferable to position at least a number of the apertures 84 directly underneath the short U.V. lamps 78 in order to further facilitate the maintenance of a proper operating temperature for the lamps 78.

AUDIO CONSOLE

Referring now to FIG. 8, the audio console 84 therein shown is generally comprised of a substantially rigid and quality acoustic sound housing 86, such as aluminum, the housing having a pair of integral speaker sound chambers 88 formed therein and a set of controls 90 positioned in an inverted fashion substantially between the sound chambers 88. A wall (unnumbered) shown in FIG. 8 isolates each sound chamber from the remainder of the console. Positioning the control 90 in an inverted fashion allows the dial on the controls to be easily read and manuvered by an individual positioned within the tanning system.

As best shown in FIG. 2, the exterior housing 86 is adapted to secure to the underside of one end of the upper unit 16 thereby being located complementary to an individual's head positioned within the system. This arrangement enhances the sound quality received by the individual without being overridden by the noise generated by the exit fans.

The audio console 84 may also be provided with a DC system for converting alternating current from an exterior source to direct current.

Referring again to FIG. 8, the console 84 may also be provided with a convenient on-off switch 92 for selective use of the console.

The integral speaker sound chambers 88 are pentagonal in elevation producing uniquely high quality fidelity. This unique pentagonal shape is also advantageously employed to fit the console into the generally matching shape of the upper unit.

COUNTERBALANCE SYSTEM

FIG. 9 illustrates a weight counterbalance system 94. The system 94 utilizes a pair of pivot arms 96 coupled to an axle 98, by means of a key 97. (FIG. 10). The arms are mounted in parallel fashion to opposite ends of the upper unit 16.

The axle 98 extends between the arms 96. Wound around the axle at opposite ends thereof are a pair of torsion springs 102 pre-loaded to approximately 3400 pounds. The ends of the springs 104 closest to the arms 96 are fixedly attached to the frame 12, while the other ends 106 of the springs, being distal to the arms, are indirectly coupled to the axle through the use of a collar 108 locked to the axle 98 by a set screw 110.

The counterbalance requires only a light force of about five lbs. to move up or down the otherwise very heavy upper unit.

As shown in FIG. 10, in order to limit the pivotal upward and downward movement of the upper unit 16, it is preferable to provide the frame 12 with a pair of stops 112. The stop 112 to the left in FIG. 10 prevents the springs from unwinding when the top unit is lifted off the arms 96, as when shipping.

As a safety consideration, it is preferable to provide the tanning system with an emergency shut-off switch (not shown) in case of any malfunction in the normal operation of the system. Further, for esthetic purposes, the exterior of the system may be painted with a substance, such as sold under the trademark DURATHANE, which has the capacity to expand and contract with rapid temperature changes. Should the tanning system be placed in a commercial setting, it may be preferable to provide the system with a built in token operated timer designed with a hidden token counter and token drop box in separate, keyed compartments for management control and verification of equipment usage.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. An improved air circulatory system for use in a tanning system having a stationary lower unit and a movable upper unit secured to a frame, both of the units provided with a series of ultraviolet light generating lamps positioned thereon operatively connected to a series of ballasts, comprising:
    cooling air intake vents located centrally along the length of each unit; and
    a series of exit fans, said fans including at least two fans positioned at each of said opposite ends of said upper unit and said lower unit for drawing air from said central intake vents and along the interior of said upper and lower units; each said unit having an elongated channel panel, said fans at each end being spaced from one another and positioned at the ends of said channel panels; said panel having vertically extending channel side walls and a bottom wall for housing said lamps, a plurality of apertures formed in the bottom wall and positioned to concentrate air flow to the lamps in the area of the unit that generates the maximum heat for aiding the lamps to be energized at a generally constant temperature.

2. The system of claim 1, including a plurality of air baffles positioned at the longitudinal ends of the most laterally spaced lamps for diverting air flow transversely centrally inwardly to concentrate the cooling air flow to more centrally located lamps.

3. The system of claim 1, said ballasts generating undesirable heat, the ballasts on said lower unit abutting the frame, said frame comprising a high heat conductive metal shell for creating a cooling heat sink for said ballasts to dissipate heat generated by said ballasts.

4. The air circulatory system as defined in claim 1 including a set of filters positioned contiguous to a corresponding intake vent.

5. The system of claim 1, said intake upper unit having a single intake vent positioned rearwardly on the unit, the air flow entering the vents and dividing equally to exit through the fans at opposite ends.

6. The system of claim 1, including at least three fans positioned at each of said opposite ends of said upper and lower unit at the ends of said channel panels, each of said three fans at each end of said channel panel being equidistantly spaced from one another.

7. An improved air circulatory system for use in a tanning system having a stationary lower unit and a movable upper unit secured to a frame, both of the units provided with a series of ultraviolet light generating lamps positioned thereon operatively connected to a series of ballasts, comprising:
    cooling air intake vents located centrally along the length of each unit, each of said intake vents having a filter positioned contiguous thereto;
    a series of exit fans, said fans positioned at opposite ends of said upper unit and said lower unit for drawing air from said central intake vents along the interior of said upper and lower units; each said unit having an elongated channel panel, said panel having vertically extending channel side walls and a bottom wall for housing said lamps, a plurality of apertures formed in the bottom wall and positioned to concentrate airflow to the lamps in the area of the unit that generates the maximum heat for aiding the lamps to be energized at a generally constant temperature;
    a plurality of air baffles positioned at the longitudinal ends of the most laterally spaced lamps for diverting airflow transversely centrally and inwardly to concentrate the cooling air flow to more centrally located lamps; and
    ballasts on said lower unit abutting the frame, said frame comprising a high heat conductive metal shell for creating a cooling heat sink for said ballast to dissipate heat generated by said ballast, said ballasts on said lower unit spaced from one another to define a void in the longitudinal center of the unit for minimizing ballast generated heat adjacent the buttocks engaging region of the lower unit.

8. An improved air circulatory system for use in a tanning system having a stationary lower unit and a movable upper unit secured to a frame, both of the units provided with a series of ultraviolet light generating lamps positioned thereon operatively connected to a series of ballasts, comprising:
    cooling air intake vents located centrally along the length of each unit; and
    a series of exit fans, said fans positioned at oppoosted ends of said upper unit and said lower unit for drawing air from said central intake vents and along the interior of said upper and lower units; each said unit having an elongated channel panel, said panel having vertically extending channel side walls and a bottom wall fro housing said lamps, a plurality of apertures formed in the bottom wall and positioned to concentrate air flow to the lamps in the area of the unit that generates the maximum heat for aiding the lamps to be energized at a generally constant temperature, and wherein said ballasts on said lower unit are spaced from one another to define a void in the longitudinal center of the unit for minimizing ballast generated heat adjacent the buttocks engaging region of the lower unit.

* * * * *

UNITED STATES PATENT AND TRADEMARK OFFICE
CERTIFICATE OF CORRECTION

PATENT NO. : 4,683,887
DATED : August 4, 1987
INVENTOR(S) : Sharon D. Kramer; John Kramer; Donald Kramer; Clark Kramer It is certified that error appears in the above—identified patent and that said Letters Patent is hereby corrected as shown below:

In Claim 1, line 20, delete "air flow" and substitute therefor --airflow--.

In Claim 7, line 25, delete "air flow" and sustitute therefor --airflow--.

In Claim 8, line 15, delete "fro" and substitute therefor --for--.

Signed and Sealed this

Twenty-sixth Day of April, 1988

Attest:

DONALD J. QUIGG

*Attesting Officer*   *Commissioner of Patents and Trademarks*